United States Patent [19]

Endres et al.

[11] Patent Number: 5,044,367
[45] Date of Patent: Sep. 3, 1991

[54] METHOD AND APPARATUS FOR SWITCHING CARDIAC STIMULATION SIGNALS

[75] Inventors: William P. Endres; Betty Stephens, both of Portland, Oreg.

[73] Assignee: The State of Oregon Acting by and Through the State Board of Higher Education on Behalf of Oregon Health Sciences University, Portland, Oreg.

[21] Appl. No.: 371,495

[22] Filed: Jun. 26, 1989

[51] Int. Cl.$^5$ .............................................. A61N 1/08
[52] U.S. Cl. ............................ 128/419 R; 128/419 P; 128/419 D
[58] Field of Search ........ 128/419 P, 419 PG, 419 D, 128/419 R, 419 S, 709

[56] References Cited

U.S. PATENT DOCUMENTS

| | | | |
|---|---|---|---|
| 4,462,406 | 7/1984 | DeCote, Jr. | 128/419 PG |
| 4,554,928 | 11/1985 | Webster, Jr. | 128/419 PG |
| 4,735,206 | 4/1988 | Hewson | 128/419 PG |

OTHER PUBLICATIONS

Schwigshackl et al., "Digital System for Artificial Fibrillation of Animal Hearts," Biomed. Engr., vol. 8, No. 11, 11–1973.
Jaros et al., "New Approaches to Fibrillation and Defibrillation of the Heart," S. A. Medical Journal, 1–1972, pp. 63–67.
Rastelli et al., "External Defib. with Thorax Open," Journal of Thoracic & Cardiovascular Surg., vol. 55, No. 1, 1–1968.
Hopps et al., "Recent Advances in Surgery," vol. 36, No. 4, 10–1954, pp. 833–849.

*Primary Examiner*—William E. Kamm
*Assistant Examiner*—Kennedy J. Schaetzle
*Attorney, Agent, or Firm*—Klarquist, Sparkman, Campbell, Leigh & Whinston

[57] ABSTRACT

Cardiac stimulation signals are routed through a switching network to select only one cardiac stimulation signal as an output signal. The selected output signal may be routed to one of two patient electrode pairs for application to specific stimulation sites on the heart.

15 Claims, 2 Drawing Sheets

METHOD AND APPARATUS FOR SWITCHING CARDIAC STIMULATION SIGNALS

Background of the Invention

The heart pumps blood by organized successive contraction of individual heart muscle fibers. A neurological signal spreads through the heart and each muscle fiber responds by contracting in sequence. The overall effect is a single heart beat or heart pulse moving blood through the heart. For effective pumping the fibers must contract in an organized fashion. When the fibers contract in a disorganized fashion the heart does not pump blood. This condition is called fibrillation.

Control of cardiac activity by electric signal has proven to be useful during heart surgery. In some instances it is necessary to maintain a constant pulse rate by application of a pacing signal to the heart. The pacing signal provides an electric pulse initiating organized contraction of the heart muscle fibers throughout the heart and stimulating a single heart beat. A pacing signal presented as a series of such electric pulses at regular intervals maintains a regular heart beat. Thus, a pacing signal is a regulating signal for maintaining constant and effective pumping action by the heart.

In other instances, it is necessary to temporarily stop the heart by application of a fibrillation signal to the heart. The fibrillation signal is a low voltage AC signal disrupting the normal organized contraction of individual heart muscle fibers. The fibrillation signal forces the heart into a state of fibrillation where the heart essentially stops pumping blood. A heart/lung machine oxygenates and pumps blood during application of the fibrillation signal. At certain times during surgery fibrillation of the heart is advantageous. For example, while performing coronary by-pass surgery it is very difficult to cut a beating heart. Also, when a vein or artery is opened it is desirable that the heart be in a state of fibrillation to avoid excess loss of blood through the open vein or artery.

A pacing signal and a fibrillation signal have opposite effects on the heart. The pacing signal causes pumping by the heart and the fibrillation signal stops pumping by the heart. Accordingly, it is of great importance that these signals be applied exclusively with respect to one another.

In a typical surgical operation a fibrillation signal generator connects to the heart by a pair of fibrillation electrodes, a positive conductor and a negative conductor. A pacing signal generator also connects to the heart by a separate pair of pacing electrodes, a positive conductor and a negative conductor. When the surgeon wishes to pace the heart, the surgeon turns on the pacing signal generator and the heart receives a pacing signal. When the surgeon wishes to stop the heart, the surgeon turns off the pacing signal generator and turns on the fibrillation signal generator. The heart then receives a fibrillation signal. An operating room is a very busy place. When a pacing machine and a fibrillation machine are connected to the patient there is no absolute guarantee that both signals will be applied exclusively with respect to one another. The possibility exists for both the pacing machine and the fibrillation machine to be on and concurrently applying their respective signals to the patient's heart.

It is therefore desirable to ensure against the possibility of the heart receiving both a pacing signal and a fibrillation signal.

Summary of the Invention

A cardiac stimulation device includes a first cardiac stimulation signal source and a second cardiac stimulation signal source. A switching network selects one of the cardiac stimulation signals as a selected output signal. The switching network also routes the selected output signal to one of a number of output jack pairs. Each output jack pair connects by patient electrodes to different stimulation sites on the heart. The switching network ensures that one and only one of the cardiac stimulation signals reaches the heart at any given time. The switching network also enables selection among the different output jack pairs to select different stimulation sites.

In a preferred embodiment of the present invention, the first cardiac stimulation signal source is a fibrillation signal generator including a transformer and potentiometer for adjusting the amplitude of the low voltage AC fibrillation signal. The second cardiac stimulation signal source is a connector adapted to receive a pacing signal from an external separate or pacing signal generator.

In alternative embodiments the device includes two internal signal generators one for pacing and one for fibrillation, two connectors for connection to two external signal generators, or some combination of input connectors and signal generators. In any case, the device ensures that the cardiac stimulation signals are applied to the heart exclusively with respect to one another. The signals cannot be applied concurrently.

Accordingly, it is an object of the present invention to provide an apparatus for applying a plurality of cardiac stimulation signals to a heart by way of a plurality of patient electrodes while ensuring that the signals are not applied concurrently and while allowing selection among the patient electrodes.

The subject matter of the present invention is particularly pointed out in the concluding portion of this specification. Both the organization and method of operation of the invention, together with further advantages and objects thereof, however, may best be understood by reference to the following description and accompanying drawings wherein like reference characters refer to like elements.

Detailed Description of the Invention

Figure 1:
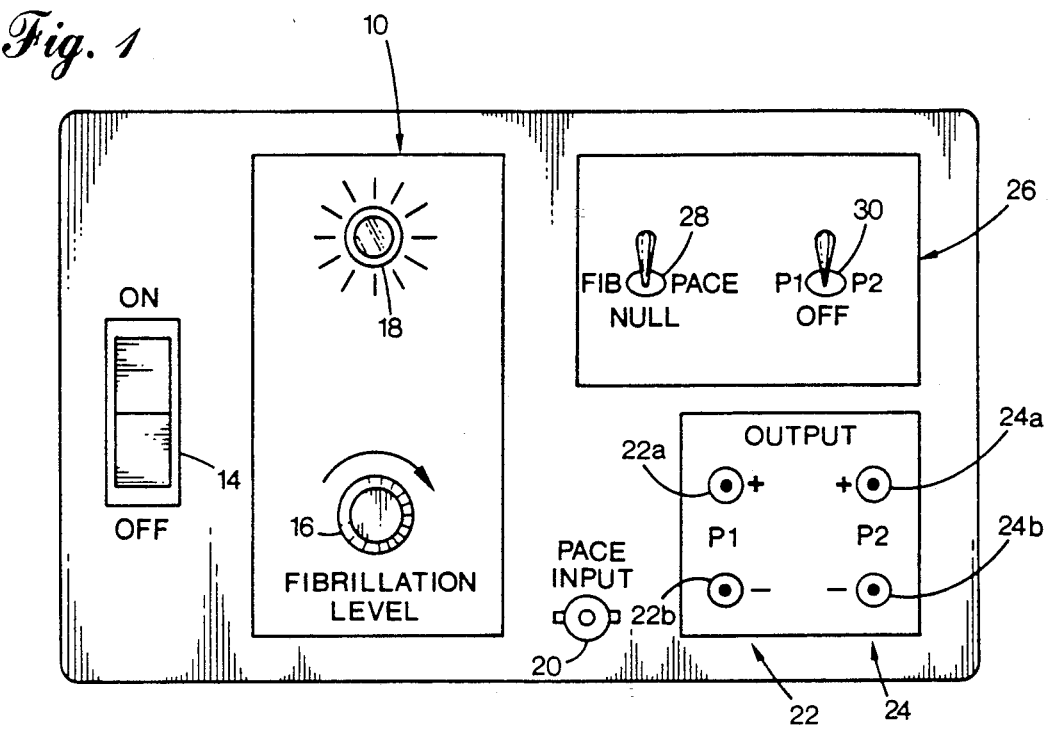
FIG. 1 is a plan view of a control panel of a cardiac stimulation device according to the present invention.
Figure 2:
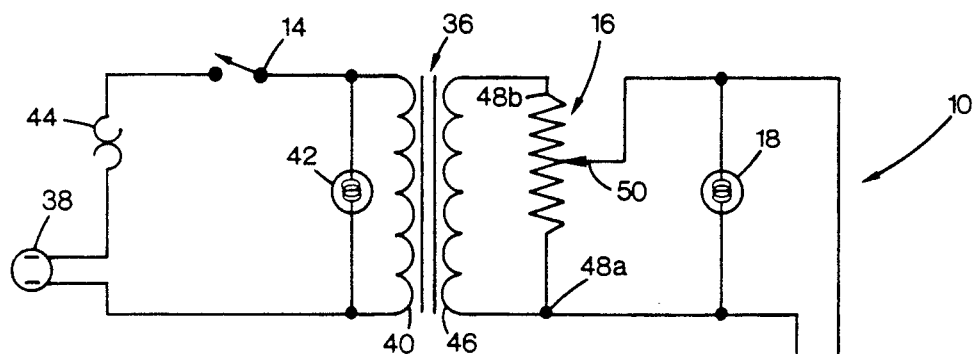
FIG. 2 is a schematic diagram of the device of FIG. 1.
Figure 2:
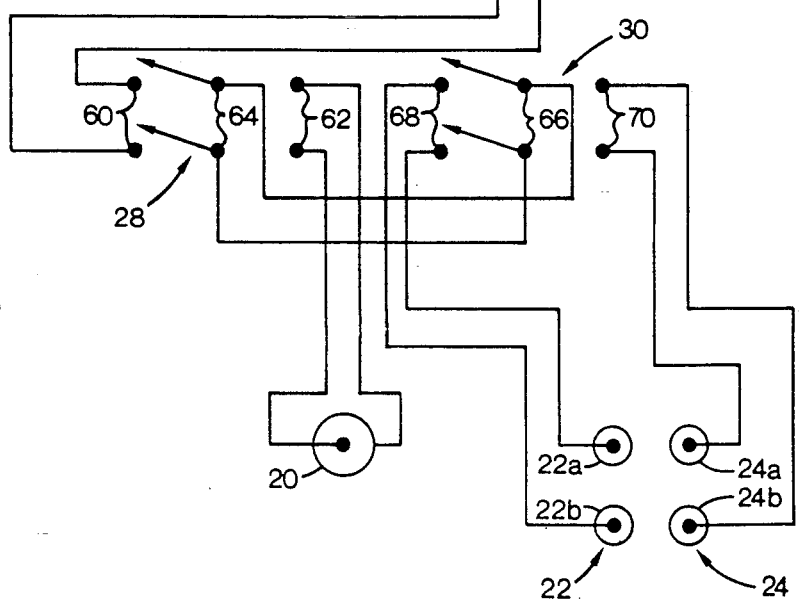

FIGS. 1 and 2 illustrate a preferred embodiment of the present invention. The preferred embodiment includes a fibrillation signal generator 10 receiving AC power by way of power switch 14 and providing an adjustable low voltage AC fibrillation signal. Control 16 determines the fibrillation signal level. The brightness of lamp 18 provides a visual indication of the fibrillation signal level. Input BNC jack 20 carries two conductors and receives a pacing signal from a separate pacing signal generator (not shown). Output jack pair 22, including positive conductor 22a and negative conductor 22b, and output jack pair 24, including positive conductor 24a and negative conductor 24b, each connect to separate patient electrode sets (not shown). A pacing signal or a fibrillation signal may be delivered to the patient's heart tissue by either electrode set. Switching network 26 selects an output signal and which of output jack pairs 22 and 24 provide the output signal. Switch 28 selects either the pacing signal, the fibrillation signal, or a null signal as a selected output signal. Switch 30 routes the selected output signal to output jack pair 22, to output jack pair 24, or to neither of output jack pairs 22 and 24.

During surgery up to two electrode sets may be used to attach to different stimulation sites on the heart. A first electrode set attaches to output jack pair 22 and a second electrode set attaches to output jack pair 24. Switch 28 determines whether the patient receives a pacing signal, a fibrillation signal, or no signal. Switch 30 determines where, i.e. which stimulation site, the selected signal is delivered.

Because the pacing signal and the fibrillation signal are both routed through a single switching network, the signals are applied exclusively with respect to one another. The possibility of a patient receiving both signals concurrently is eliminated.

FIG. 2 is a schematic diagram of the preferred embodiment of the present invention. Fibrillation signal generator 10 includes a transformer 36 and an AC power plug 38. Plug 38 receives 120 volt line voltage from an AC power receptacle (not shown) and delivers the 120 volt AC power to primary winding 40 of transformer 36. Power switch 14 connects in series between one leg of plug 38 and one end of winding 40 to de-couple transformer 36 from the AC power source. Lamp 42, serving as a backlight for power switch 14, connects across the ends of winding 40 to indicate application of power to fibrillation signal generator 10. Fuse 44 connects in series with power switch 14 to de-couple fibrillation signal generator 10 from the AC power source in appropriate circumstances.

Transformer 36 steps down the 120 volt line voltage to approximately 7 volts across secondary winding 46. Control 16 is a potentiometer with its stationary terminals 48a and 48b connected in parallel with winding 46. Control 16 acts as a voltage divider to provide scaled version of the AC signal present on winding 46. Thus, an adjustable fibrillation signal ranging between approximately zero and seven volts appears across movable terminal 50 and stationary terminal 48a of control 16. Lamp 18 connects in parallel across terminals 50 and 48a and varies in brightness according to the voltage level of the fibrillation signal.

Switch 28 is a double-throw double-pole center off toggle switch. A first pole set 60 of switch 28 connects one-to-one to terminals 50 and 48a of control 16 to receive the fibrillation signal. A second pole set 62 of switch 28 connects one-to-one to each the two conductors of input BNC jack 20 to receive the pacing signal. Switch 28 has three positions. In the first position, pole set 60 connects to a center pole set 64 of switch 28 thereby routing the fibrillation signal to center pole set 64. In a second position, pole set 62 connects to center pole set 64 to route the pacing signal from jack 20 to center pole set 64. The third or center-off position isolates center pole set 64 from pole sets 60 and 62 such that a null signal, i.e. no signal, is present at center pole set 64. Thus, operation of switch 28 determines what signal is selected for output. Either the pacing signal, the fibrillation signal, or a null signal is selected as an output signal. It is not possible to select both the fibrillation signal and the pacing signal concurrently. If a pacing signal is not applied to input jack 20, a null signal is selected for output in the second and third positions of switch 28.

Switch 30 is also a double-throw double-pole center off toggle switch. Center pole set 66 of switch 30 connects to center pole set 64 of switch 28. The selected output signal is then present at center pole set 66. Switch 30 determines whether the selected output signal is routed to output jack pairs 22 and 24, and if so routed which of jack pairs 22 and 24 receives the selected output signal. Pole set 68 of switch 30 connects one-to-one to conductors 22a and 22b. Pole set 70 of switch 30 connects one-to-one to conductors 24a and 24b. Switch 30 has three positions. The first position connects center pole set 66 to pole set 68 to route the selected output signal to output jack pair 22. The second position connects center pole set 66 to pole set 70 to route the selected output signal to output jack pair 24. The third or center-off position isolates center pole set 66 to prevent coupling of the selected output signal to either of output jack pairs 22 and 24.

In overall operation, power switch 14 is first turned off and plug 38 is attached to a power receptacle. The surgeon attaches a first electrode pair to jack pair 22 and to a first stimulation site on the patient's heart. If a second electrode pair is needed, the surgeon attaches the second electrode pair to jack pair 24 and to a second stimulation site on the patient's heart. Switch 28 is placed in its center-off position to select a null signal as output. Switch 30 is also placed in its center-off position to block passage of the selected output signal to either of output jack pairs 22 and 24. A separate pacing signal generator is connected to input jack 20. The pacing signal generator may be turned on such that the pacing signal appears at pole set 62 of switch 28. Power switch 14 is then placed in its on position to energize transformer 36 and provide a fibrillation signal to pole set 60 of switch 28.

During surgery, switches 28 and 30 are normally left in their center off positions. But, the surgeon can apply either the fibrillation signal or the pacing signal to the patients heart. The surgeon must first select one of the signals as an output signal by operation of switch 28. The surgeon then routes the selected signal to one of the electrode pairs by operation of switch 30. It is not possible to apply both signals concurrently. The surgeon can alternate stimulation sites by moving switch 30 between its first and second positions.

In the preferred embodiment of the present invention, a fibrillation signal generator is included in the device and a pacing signal is received from a separate device. However, the scope of the present invention includes other configurations for routing cardiac stimulation signals to patient electrodes.

Figure 3:
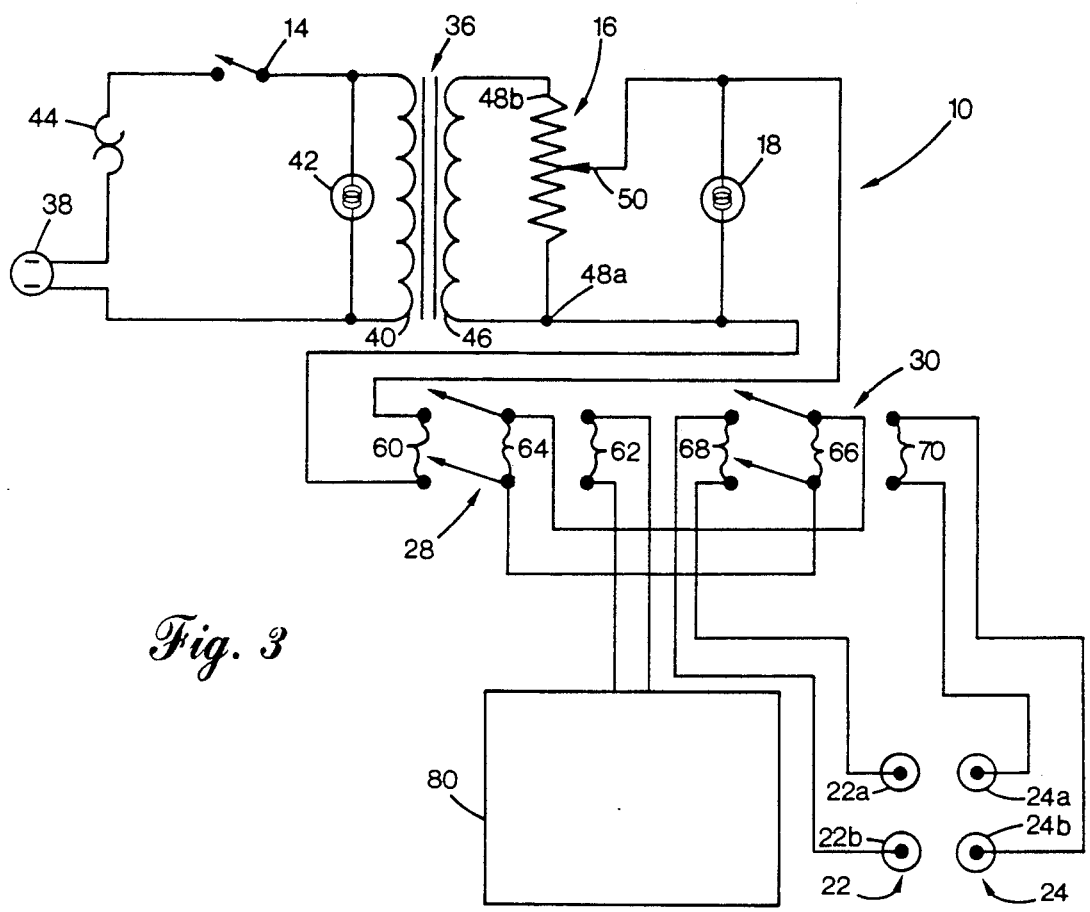
FIGS. 3 and 4 are schematic diagrams of alternative embodiments of the present invention.

In FIG. 3, input BNC jack 20 is replaced by a pacing signal generator 80. In this configuration no external device is required. Fibrillation signal generator 10 provides a fibrillation signal to pole set 60 of switch 28. Pacing signal generator 80 provides a pacing signal to pole set 62 of switch 28. Switches 28 and 30 operate as described above to select an output signal and determine which of output jack pairs 22 and 24 receive the selected output signal.

Figure 4:
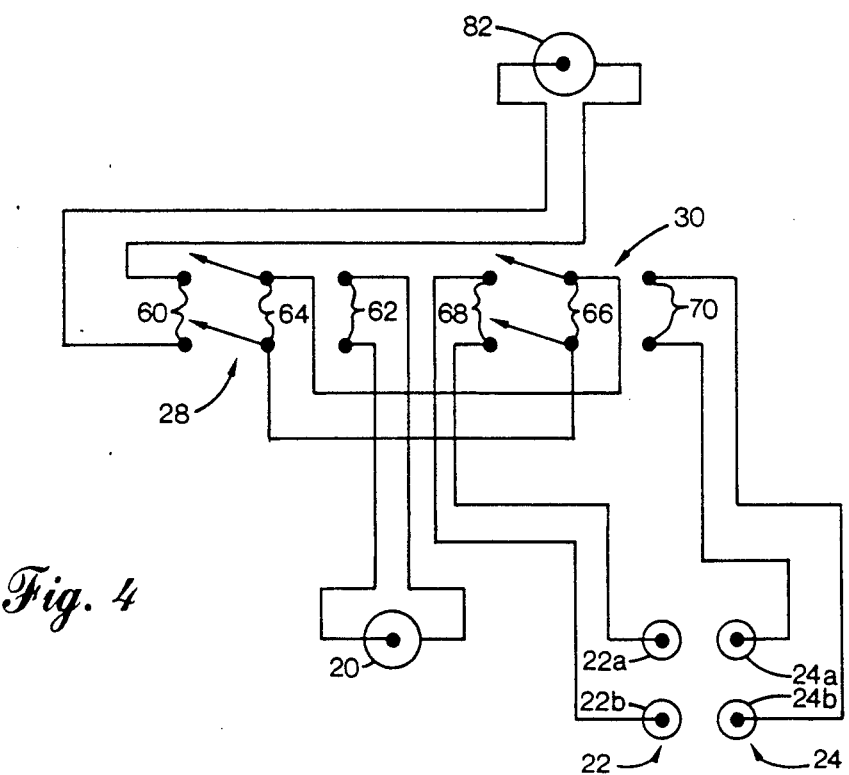

In FIG. 4, fibrillation signal generator 10 is replaced by input jack 82. In this configuration a pacing signal is provided to jack 20 by a separate pacing signal generator. A separate fibrillation signal generator provides a fibrillation signal at BNC input jack 82. Pole set 60 of switch 28 connect one-to-one to the two conductors of input jack 82. Switches 28 and 30 operate as described above to select and route a cardiac stimulation signal to one of output jack pairs 22 and 24.

While a preferred embodiment and several alternative embodiments of the present invention have been shown and described, it will be apparent to those skilled in the art that many changes and modifications may be made without departing from the invention in its broader aspects. The appended claims are therefore intended to cover all such changes and modifications as fall within the true spirit and scope of the invention.

I claim:

1. An apparatus for selectively applying first and second cardiac stimulation signals to a human or other animal subject via an electrode pair, the apparatus comprising:
   first means for receiving a first cardiac stimulation signal;
   second means for receiving a second cardiac stimulation signal;
   switching means, coupled to said first and second means, for selectively providing only one of the first and second cardiac stimulation signals as a selected output signal;
   output means coupled to said switching means for applying the selected output signal to an electrode pair, said output means including first and second electrode connector pairs; and
   said switching means comprising a first switch coupled to said means for receiving the first cardiac stimulation signal and to said means for receiving the second cardiac stimulation signal, said first switch selecting one of the first cardiac stimulation signal and the second cardiac stimulation signal or a null signal as the selected output signal, and a second switch receiving the selected output signal and operative to route the selected output·signal to one of said first and second electrode connector pairs.

2. An apparatus according to claim 1 wherein said apparatus further comprises means for generating the first cardiac stimulation signal, said means for generating the first cardiac stimulation signal being coupled to said means for receiving the first cardiac stimulation signal.

3. An apparatus according to claim 1 wherein said means for receiving the first cardiac stimulation signal comprises a connector adapted for coupling to a first cardiac stimulation signal generator.

4. An apparatus according to claim 1 further comprising a plurality of connector means each adapted for coupling to separate patient electrode pairs, and wherein said switching means comprises means for routing the selected output signal to one of said plurality of connector means.

5. An apparatus according to claim 1 wherein said first cardiac stimulation signal is a fibrillation signal and said second cardiac stimulation signal is a pacing signal.

6. In combination,
   means for receiving a pacing signal,
   a fibrillation signal generator providing a fibrillation signal as output,
   a switching network coupled to said means for receiving the pacing signal and to said fibrillation signal generator for selecting one of said pacing signal and said fibrillation signal as a selected output signal;
   connector means coupled to said switching network to receive the selected output signal, said connector means being adapted for coupling to a patient electrode pair, and including a plurality of separate connector jack pairs, each connector jack pair being adapted for connection to separate patient electrode pairs, and wherein said switching network comprises means for routing the selected output signal to one of said connector jack pairs.

7. A combination according to claim 6 wherein the combination further comprises a pacing signal generator coupled to said means for receiving the pacing signal.

8. A combination according to claim 6 wherein said switching network comprises a first switch for selecting one of the pacing signal and the fibrillation signal as the selected output signal, and a second switch coupled to said first switch for delivering the selected output signal to one of said connector jack pairs.

9. Apparatus for selectively applying one of a pacing signal and a fibrillation signal to one of a first patient electrode pair and a second patient electrode pair, the apparatus comprising:
   a transformer adapted for connecting to a source of AC power and providing a stepped-down AC signal;
   amplitude adjustment means for receiving said stepped-down AC signal, adjustably attenuating the amplitude of the stepped-down AC signal, and providing the attenuated stepped-down AC signal as the fibrillation signal;
   means for receiving the pacing signal;
   a first switch having a first pole set coupled to said amplitude adjustment means to receive the fibrillation signal, a second pole set connected to said receiving means to receive the pacing signal, and a center pole set providing a selected output signal whereby a first position of said first switch connects the first pole set to the center pole set to provide the fibrillation signal as the selected output signal, a second position of said first switch connects the second pole set to the center pole set to provide the pacing signal as the selected output signal, and a third position of said first switch isolates the center pole set from the first and second pole sets and provides a null signal as the selected output signal;
   a second switch having a first pole set, a second pole set, and a center pole set, the center pole set of said first switch being connected to the center pole set of said second switch whereby a first position of said second switch connects the center pole set of said second switch to the first pole set of said second of said second switch, a second position of said second switch connects the center pole set of said second switch to the second pole set of said second switch, and a third position of said second switch isolates the center pole set of said second switch from the first and second pole sets of said second switch;
   first output connector means connected to the first pole set of said second switch and adapted for coupling to said first patient electrode pair; and second output connector means connected to the second pole set of said second switch and adapted for coupling to said second patient electrode pair.

10. An apparatus according to claim 9 wherein said means for receiving the pacing signal comprises a connector adapted for coupling to a pacing signal generator.

11. An apparatus according to claim 9 wherein said amplitude adjustment means comprises an adjustable voltage divider connected to a secondary winding of said transformer.

12. A method of stimulating hear tissue by electric signal, the method comprising the steps:
providing first and second cardiac stimulation signals;
routing said first and second cardiac stimulation signals through a switching network for selecting one of said first and second cardiac stimulation signals as a selected output signal; and
applying the selected output signal to a connector pair adapted for coupling to a patient electrode pair by routing the selected output signal through a second switching network for routing the selected output signal to one of two connector pairs each adapted for coupling to separate patient electrode pairs.

13. A method according to claim 12 wherein said step of providing first and second cardiac stimulation signals includes the steps of generating one of said first and second cardiac stimulation signals and receiving the other one of said first and second cardiac stimulation signals by connector means.

14. A method according to claim 12 wherein said first cardiac stimulation signal causes said heart tissue to substantially stop pumping blood and said second cardiac stimulation signal causes said heart tissue to pump blood at a regulated pace.

15. A method according to claim 12 wherein the first cardiac stimulation signal is a fibrillation signal and the second cardiac stimulation signal is a pacing signal.

* * * * *